United States Patent
Sorrenti et al.

(10) Patent No.: US 8,361,080 B2
(45) Date of Patent: Jan. 29, 2013

(54) IMPLANT INSERTER HAVING A BIFURCATED ADJUSTABLE STOP

(75) Inventors: Michael D. Sorrenti, Marlboro, MA (US); Edward Zalenski, Lakeville, MA (US)

(73) Assignee: DePuy Spine, Inc., Raynham, MA (US)

( * ) Notice: Subject to any disclaimer, the term of this patent is extended or adjusted under 35 U.S.C. 154(b) by 1015 days.

(21) Appl. No.: 11/694,608

(22) Filed: Mar. 30, 2007

(65) Prior Publication Data

US 2008/0243131 A1    Oct. 2, 2008

(51) Int. Cl.
*A61B 17/56* (2006.01)
(52) U.S. Cl. ............ 606/99; 623/17.16
(58) Field of Classification Search .......... 606/99, 606/104, 90, 100, 86 A
See application file for complete search history.

(56) References Cited

U.S. PATENT DOCUMENTS

| | | | |
|---|---|---|---|
| 4,957,495 A | 9/1990 | Kluger | |
| 5,352,231 A | 10/1994 | Brumfield | |
| 6,332,887 B1 | 12/2001 | Knox | |
| 6,436,102 B1 | 8/2002 | Ralph | |
| 6,554,864 B2 | 4/2003 | Ralph | |
| 6,562,047 B2 | 5/2003 | Ralph | |
| 6,607,559 B2 | 8/2003 | Ralph | |
| 6,616,666 B1 | 9/2003 | Michelson | |
| 6,648,891 B2 | 11/2003 | Kim | |
| 6,663,638 B2 | 12/2003 | Ralph | |
| 6,712,818 B1 | 3/2004 | Michelson | |
| 6,740,087 B2 | 5/2004 | Knox | |
| 6,805,716 B2 | 10/2004 | Ralph | |
| 2004/0215198 A1 | 10/2004 | Marnay et al. | |
| 2004/0220582 A1* | 11/2004 | Keller | 606/99 |
| 2004/0225295 A1* | 11/2004 | Zubok et al. | 606/90 |
| 2004/0267275 A1* | 12/2004 | Cournoyer et al. | 606/99 |
| 2005/0021042 A1* | 1/2005 | Marnay et al. | 606/99 |
| 2005/0033305 A1* | 2/2005 | Schultz | 606/99 |
| 2005/0090824 A1* | 4/2005 | Shluzas et al. | 606/61 |
| 2005/0228400 A1* | 10/2005 | Chao et al. | 606/104 |
| 2005/0256575 A1* | 11/2005 | Pavlov et al. | 623/17.11 |
| 2006/0025777 A1* | 2/2006 | Weber | 606/99 |

\* cited by examiner

*Primary Examiner* — Thomas Barrett
*Assistant Examiner* — Michael T Schaper

(57) ABSTRACT

A spinal implant insertion tool, comprising: a) a shaft having distal end having upper and lower pairs of prongs extending therefrom, the prongs adapted for holding an implant or an implant trial and defining a centerline therebetween, and b) an adjustable stop slidably received upon the shaft of the tool, wherein the adjustable stop has a bifurcated distal end defining first and second prongs that are off-centerline from the centerline. Because the stop is bifurcated and thereby avoids the centerline of the vertebral bodies, it will not collide with components of a Caspar distractor.

14 Claims, 4 Drawing Sheets

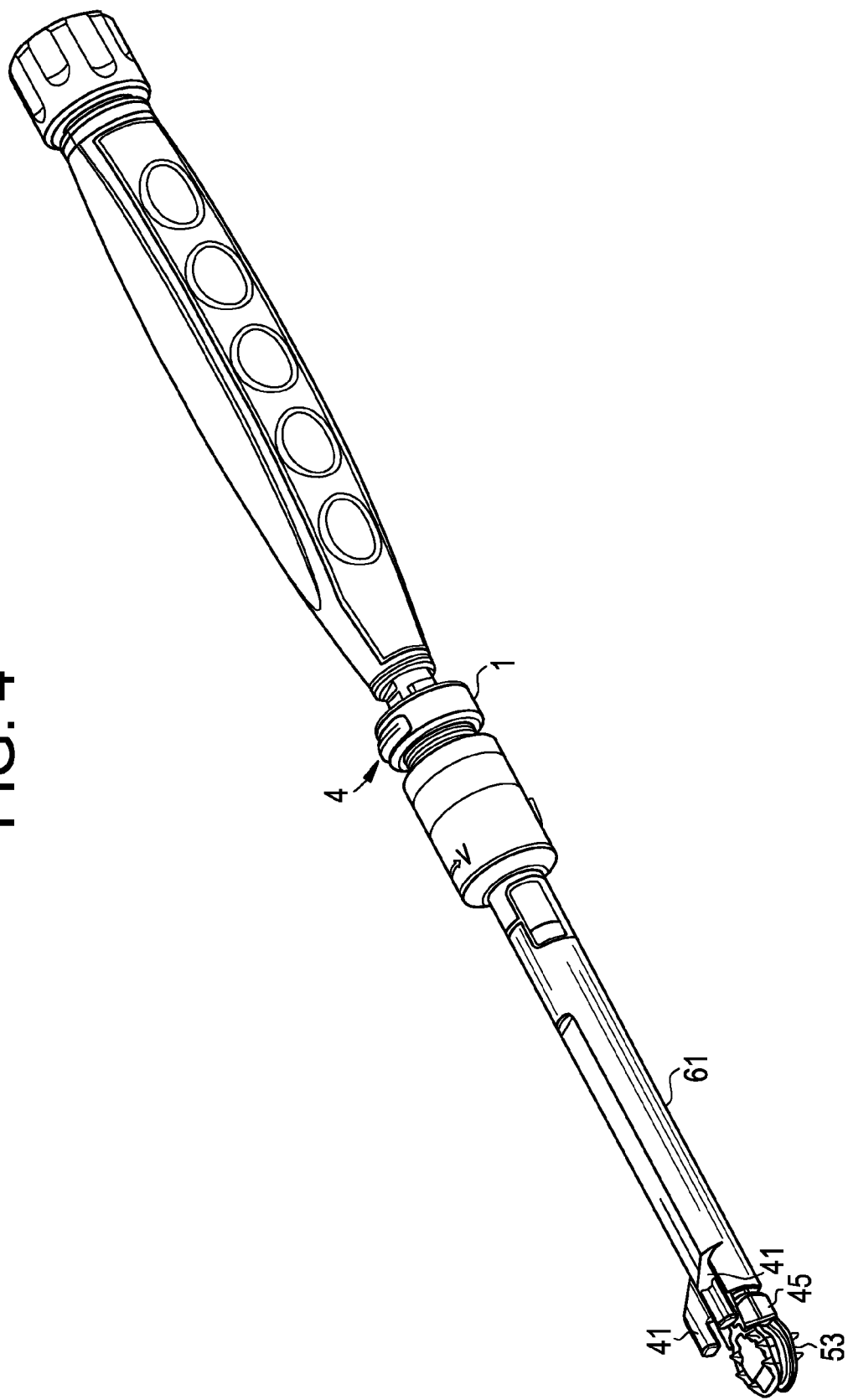

IMPLANT INSERTER HAVING A BIFURCATED ADJUSTABLE STOP

BACKGROUND OF THE INVENTION

The natural intervertebral disc contains a jelly-like nucleus pulposus surrounded by a fibrous annulus fibrosus. Under an axial load, the nucleus pulposus compresses and radially transfers that load to the annulus fibrosus. The laminated nature of the annulus fibrosus provides it with a high tensile strength and so allows it to expand radially in response to this transferred load.

In a healthy intervertebral disc, cells within the nucleus pulposus produce an extracellular matrix (ECM) containing a high percentage of proteoglycans. These proteoglycans contain sulfated functional groups that retain water, thereby providing the nucleus pulposus with its cushioning qualities. These nucleus pulposus cells may also secrete small amounts of cytokines as well as matrix metalloproteinases (MMPs). These cytokines and MMPs help regulate the metabolism of the nucleus pulposus cells.

In some instances of disc degeneration disease (DDD), gradual degeneration of the intervertebral disc is caused by mechanical instabilities in other portions of the spine. In these instances, increased loads and pressures on the nucleus pulposus cause the cells within the disc (or invading macrophages) to emit larger than normal amounts of the above-mentioned cytokines. In other instances of DDD, genetic factors or apoptosis can also cause the cells within the nucleus pulposus to emit toxic amounts of these cytokines and MMPs. In some instances, the pumping action of the disc may malfunction (due to, for example, a decrease in the proteoglycan concentration within the nucleus pulposus), thereby retarding the flow of nutrients into the disc as well as the flow of waste products out of the disc. This reduced capacity to eliminate waste may result in the accumulation of high levels of toxins that may cause nerve irritation and pain.

As DDD progresses, toxic levels of the cytokines and MMPs present in the nucleus pulposus begin to degrade the extracellular matrix. In particular, the MMPs (as mediated by the cytokines) begin cleaving the water-retaining portions of the proteoglycans, thereby reducing its water-retaining capabilities. This degradation leads to a less flexible nucleus pulposus, and so changes the loading pattern within the disc, thereby possibly causing delamination of the annulus fibrosus. These changes cause more mechanical instability, thereby causing the cells to emit even more cytokines, typically thereby upregulating MMPs. As this destructive cascade continues and DDD further progresses, the disc begins to bulge ("a herniated disc"), and then ultimately ruptures, causing the nucleus pulposus to contact the spinal cord and produce pain.

Recently, there have been attempts to manage spinal disc degeneration by removing the problematic disc and replacing it with an articulating intervertebral motion disc.

When the problematic disc is a cervical disc, many of the candidate prostheses are two-piece intervertebral motion discs having an articulation interface.

US Published Patent Application No. 2006/0025777 (Weber) discloses a spinal implant inserter having an adjustable stop. However, the Weber stop is located along the midline of the inserter, such that it essentially lies between and above the prongs of the inserter that hold the implant. Thus, the stop will contact the vertebral body at the midline of the vertebral body. The midline nature of this adjustable stop may be problematic if the surgeon also uses a Caspar distractor, as the Caspar pins protruding from the upper and lower vertebral bodies also lie along the midline. Accordingly, it is believed that this midline-centered stop may collide with components of the Caspar distractor at the midline of the vertebral body during insertion of the implant or trial into the disc space.

US Published Patent Application No. 2004/0215198 (Marnay) discloses an implant trial having an adjustable stop mechanism. However, the Marnay stop is a single prong located off center of the midline of the inserter.

US Published Patent Application No. 2004/0220582 (Keller) discloses a spinal implant inserter having an adjustable stop. However, the Keller stop is located along the midline of the inserter.

SUMMARY OF THE INVENTION

The present inventors have developed a spinal implant inserter having a bifurcated adjustable stop. Because the stop is bifurcated and thereby avoids the centerline of the vertebral bodies, it will not collide with components of a Caspar distractor.

Therefore, in accordance with the present invention there is provided a spinal implant insertion tool, comprising:
a) a shaft having a proximal end having a handle and a distal end adapted for holding an implant or an implant trial, and
b) an adjustable stop slidably received upon the shaft of the tool,
wherein the adjustable stop has a bifurcated distal end.

DESCRIPTION OF THE FIGURES

FIG. 4 is a perspective view of the assembled adjustable stop-inserter assembly of the present invention.

DETAILED DESCRIPTION OF THE INVENTION

Figure 1:
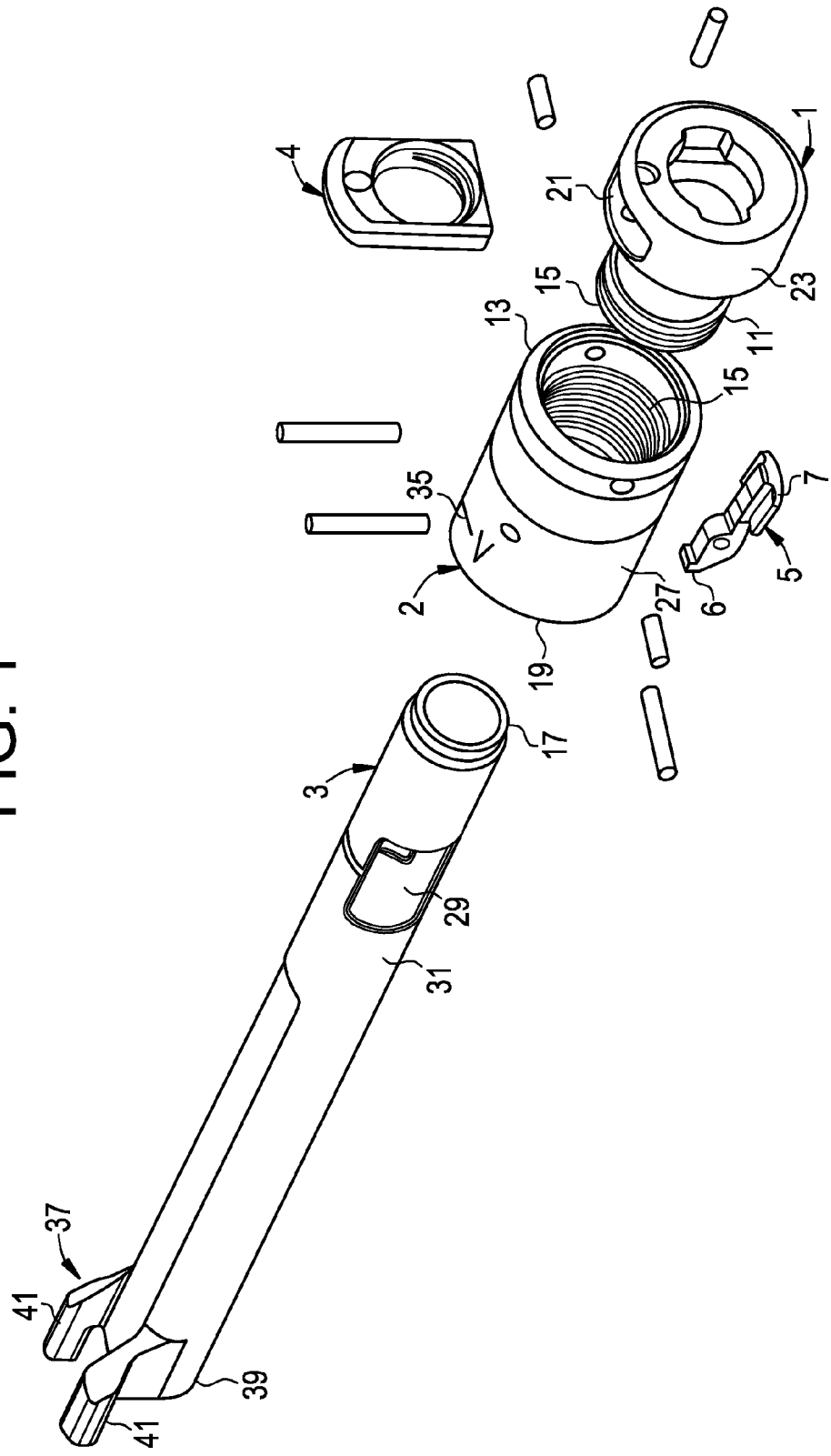
FIG. 1 is an exploded perspective view of the adjustable stop of the present invention.
Figure 2A:
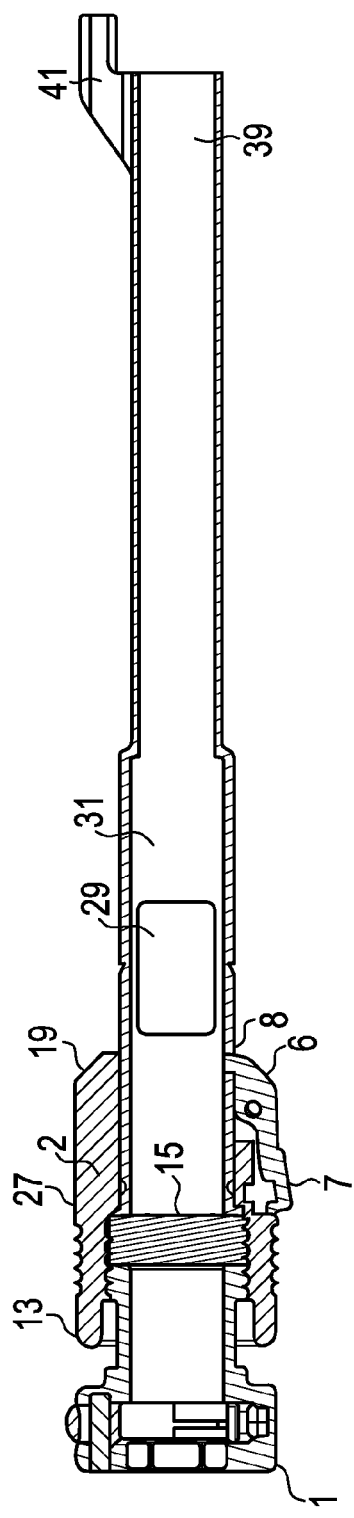
FIGS. 2a and 2b are cross-sectional and perspective views of the assembled adjustable stop of the present invention.
Figure 2B:
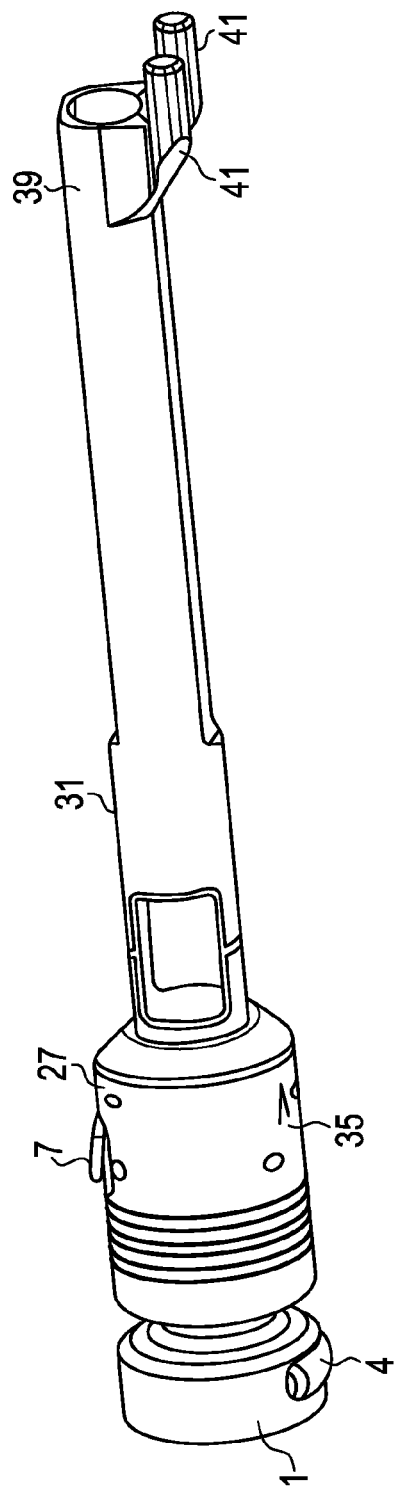

Now referring to FIGS. 1, 2a and 2b the exploded adjustable stop comprises a rotational tube 2, push button release tube 1, translation tube 3, release button 4 and locking lever 5 as its major components.

The distal end portion 11 of push button release tube 1 and the proximal end portion 13 of the rotational tube 2 have mating threadforms 15 so that the distal end portion of push button release tube 1 is threadably received in the proximal end portion of the rotational tube 2. The proximal end portion 17 of translation tube 3 is slidingly received in the distal end portion 19 of the rotational tube 2, and optionally bears against the distal end portion of the push button release tube 1.

The push button release tube has a release button 4 therein, and its distal end portion 11 is received in the rotational tube. Release button 4 is received in an opening 21 in the wall 23 of push button release tube 1. The function of the release button 4 is to alternately lock and release the shaft 25 of the inline inserter (shown in FIG. 3) to and from the adjustable stop.

Locking lever 5 is pivotally attached to the outer surface 27 of rotational tube 2 (preferably, at the distal end 19 of the rotational tube), and comprises a distal locking arm 6 and a proximal thumbpad 7. When the thumbpad is not actuated, the distal locking arm is received in a recess 8 in the outer surface 27 of the rotational tube 2, thereby locking the translational tube to the rotational tube and preventing its rotation. When its proximal thumbpad is depressed, the distal locking arm 6 of locking lever 5 rises from the recess 8, thereby unlocking translational tube 3 and freeing it for rotational movement. Rotational tube 2 should spin freely about translational tube 3 when the thumbpad 7 of locking lever 5 is depressed. In preferred embodiments, one full rotation of the rotational tube 2 about translational tube 3 causes about a 1 mm advance of the translational tube. In preferred embodiments, the locking lever is pivotally connected to the rotational tube wherein the translational tube is locked to the rotational tube when the lever is free, and the rotational tube is free to rotate about the translational tube when the lever is actuated.

Near the proximal end of the translational tube, there is preferably provided a window 29 through the wall 31 of the translational tube. This window allows the surgeon to read markings on the shaft of the interiorly situated inserter that indicate the relative position of the adjustable stop vis-à-vis the inserter.

In some embodiments, there is provided an engraved A-P arrow 35 on the translational tube of the adjustable stop. This informs the surgeon that rotating the translational tube in the clockwise direction will produce an advance of the trial in the posterior (P) direction, while rotating the translational tube in the counterclockwise direction will produce a withdrawal of the trial in the anterior (A) direction.

The adjustable stop has a bifurcated distal end 37. Typically, the adjustable stop comprises: i) a translational tube 3 adapted to be slidably received upon the shaft of the inserter tool, the translational tube having a proximal end portion 17 and a distal end portion 39, and ii) first and second prongs 41 extending radially and distally from the distal end portion of the translational tube. The bifurcated nature of the prongs allows its use with a Capsar distractor without receiving interference from the midline components of the Caspar distractor.

In preferred embodiments, the inserter component comprises a shaft 25 having a distal end portion 43 having two pair of lateral prongs 45 extending therefrom, forming upper and lower pairs of prongs. In use, these prongs clamp the implant therebetween.

Figure 3:
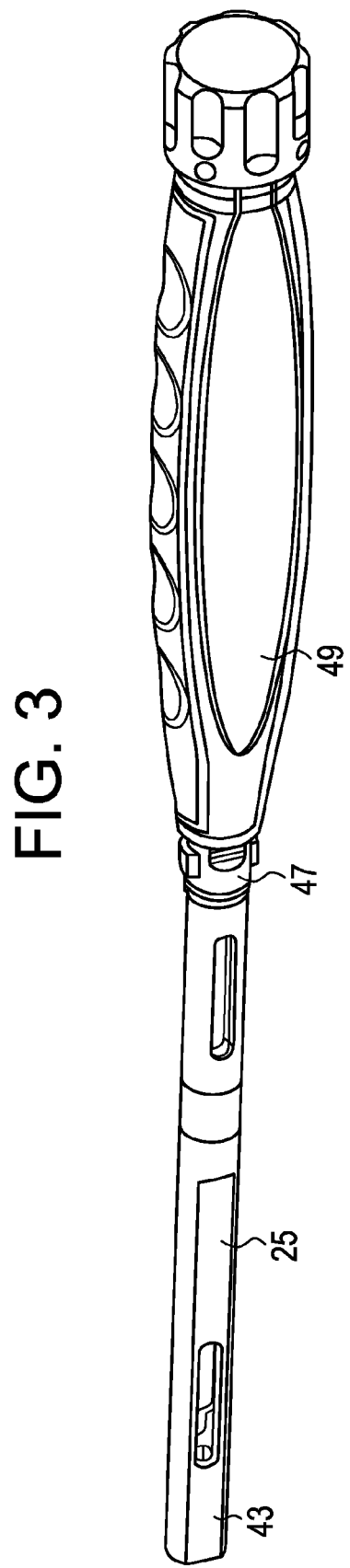
FIG. 3 is a side view of the inserter component of the present invention.

Now referring to FIGS. 3 and 4, in some embodiments, there is provided an assembly, comprising:
i) a spinal motion disc 53, and
ii) an implant insertion tool comprising:
  a) a shaft 25 having a proximal end 47 having a handle 49 and a distal end 43 having prongs 45 holding the spinal motion disc therebetween, and
  b) an adjustable stop 61 slidably received upon the shaft of the tool, wherein the adjustable stop has a pair of bifurcated prongs 41.

The motion disc component of the present invention can be any prosthetic capable of restoring the natural motions of the intervertebral disc. In preferred embodiments, the motion disc is selected from the group consisting of an articulating disc, a cushion disc and a spring-based disc.

In some embodiments, the general structure of the articulating motion disc is a two piece device (preferably designed for use in the cervical spine) and comprises:
  a) a first prosthetic vertebral endplate comprising:
    i) an outer surface adapted to mate with a first vertebral body,
    ii) an inner surface having a first articulation surface,
    iii) a body portion connecting the inner and outer surfaces,
  b) a second prosthetic vertebral endplate comprising:
    i) an outer surface adapted to mate with a second vertebral body, and
    ii) an inner surface comprising a second articulation surface,
wherein the first and second articulation surfaces are oriented produce an articulation interface.

Preferably, the articulation interfaces form partial spheres.

In some two piece designs, the second prosthetic endplate can comprise a metal component comprising the outer surface adapted to mate with a second vertebral body, and a polyethylene component comprising the inner surface comprising a second articulation surface. In some embodiments thereof, the polyethylene component could be part of the adjustable component.

In some embodiments, the general structure of the articulating motion disc is a three piece design and comprises:
a) a first prosthetic vertebral endplate comprising:
  i) an outer surface adapted to mate with a first vertebral body,
  ii) an inner surface having a first articulation surface,
  iii) a body portion connecting the inner and outer surfaces,
b) a second prosthetic vertebral endplate comprising:
  i) an outer surface adapted to mate with a second vertebral body, and
  ii) an inner surface comprising a first articulation surface,
c) a core member comprising:
  i) a first articulation surface adapted for articulation with the first articulation surface of the first endplate, and
  ii) a second articulation surface adapted for articulation with the first articulation surface of the second endplate,
wherein the core member is oriented to produce a first articulation interface between the first articulation surface of the first endplate and the first articulation surface of the core member, and a second articulation interface between the first articulation surface of the second endplate and the second articulation surface of the core member.

In some embodiments, the motion disc does not have an articulating interface. In some embodiments thereof, the motion disc is a cushion-type design having a pair of rigid endplates and a flexible center portion attached thereto. One of the endplates of this embodiment can be provided with a wedge or cam to help adjust the angle or height of the disc. In other embodiments lacking an articulating interface, the motion disc has upper and lower surfaces that articulate with the opposing natural endplates (such as a football-type design). A wedge or cam can be interpositioned between upper and lower pieces of the football-type disc to help adjust the angle or height of the disc.

The design of the adjustable stop outer tube enables it to be machined as one piece. The outer tube is machined leaving a larger diameter at the distal end. This enables the lateral prongs to be milled, which avoids welding of the prongs to the tube. Having the tube manufactured as one piece increases the long-term durability of the prong/tube junction.

In one preferred method of practicing the present invention, in order to attach the adjustable stop to the disc insertion tool, the surgeon first aligns the push-button on the push button release tube with the A/P arrow marking on the translational tube of the adjustable stop, and then aligns the two flat corresponding surfaces of the adjustable stop and the inserter, each of which are marked "superior". The surgeon then depresses the push-button and slides the adjustable stop fully over the shaft of the inserter. The surgeon then releases the push-button on the adjustable stop to lock the stop into place. Next, the surgeon sets the adjustable stop to the "0 mm" marking by depressing the thumbpad of the locking lever and rotating the rotational tube accordingly.

The surgeon then selects a disc trial that corresponds to the desired footprint and has a height that recreates the desired disc height at the operative level. The surgeon then assembles the disc insertion tool by threading the grabber tip into the cannulated end of the inserter shaft. Next, the disc trial is loaded onto the grabber tip by turning the proximal knob on the handle of the disc insertion tool. Then, under fluoroscopy, the surgeon inserts the disc trial into the disc space using the disc insertion tool. Midline placement of the disc trial is insured by inserting the disc trial in line with the vertebral distraction pins.

During trialing, the location of the adjustable stop can be adjusted by rotating the knob in accordance with the A/P arrow markings in order to change the relative A-P position of the disc trial. Lastly, the surgeon makes note of the final position of the adjustable stop obtained during trialing so that the implant can be inserted into the disc space with the same relative A-P position.

Therefore, in some embodiments, there is provided a method of implanting an intervertebral motion disc, comprising the steps of:
 a) providing the implant insertion tool of the present invention,
 b) attaching the intervertebral motion disc trial to the distal end of the shaft of the tool, and
 c) implanting the intervertebral motion disc trial in a disc space.

We claim:

1. A spinal implant insertion tool, comprising:
 a) a shaft having a proximal end having a handle and a distal end having upper and lower pairs of prongs extending therefrom, the prongs adapted for holding an implant or an implant trial and defining a centerline therebetween parallel with the shaft, and
 b) an adjustable stop slidably received upon the shaft of the tool,
 wherein the adjustable stop comprises:
 i) a translational tube adapted to be slidably received upon the shaft of the tool, the translational tube having a proximal end portion and a distal end portion, and
 ii) first and second prongs extending radially and distally from the distal end portion of the translational tube,
 iii) a rotational tube having a proximal end portion,
 iv) a release tube having a distal end portion,
 wherein the proximal end portion of the translational tube is received in the rotational tube,
 wherein the distal end portion of release tube and the proximal end portion of the rotational tube have mating threadforms so that the distal end portion of the release tube is threadably received in the proximal end portion of the rotational tube,
 and wherein the first and second prongs are off-centerline from the centerline.

2. The tool of claim 1 wherein the distal end of the shaft is adapted to hold an intervertebral motion disc selected from the group consisting of an articulating disc, a cushion disc and a spring-based disc.

3. The tool of claim 2 wherein the intervertebral motion disc is an articulating disc.

4. The tool of claim 1 wherein the distal end of the shaft is adapted to hold a multi-piece motion disc.

5. The tool of claim 4 wherein the distal end of the shaft is adapted to hold a two-piece motion disc.

6. The tool of claim 4 wherein the distal end of the shaft is adapted to hold a three-piece motion disc.

7. The tool of claim 1 wherein the upper and lower pairs of prongs are adapted to clamp the implant therebetween.

8. The tool of claim 1 wherein the translational tube has a window for viewing markings on the shaft.

9. The tool of claim 1 wherein the adjustable stop further comprises iv) a locking lever pivotally connected to the rotational tube wherein the translational tube is locked to the rotational tube when the lever is free, and the rotational tube is free to rotate about the translational tube when the lever is actuated.

10. The tool of claim 1 wherein the release tube has a release button therein.

11. The tool of claim 10 wherein the release button is adapted to hold and release the adjustable stop from the shaft of the tool.

12. A method of implanting an intervertebral motion disc trial, comprising the steps of:
 a. providing the implant insertion tool of claim 1,
 b. attaching the intervertebral motion disc trial to the distal end of the shaft of the tool, and
 c. implanting the intervertebral motion disc trial in a disc space.

13. The method of claim 12 further comprising the step of:
 d) adjusting the adjustable stop.

14. The tool of claim 1 wherein the prongs of the stop are located on an upper portion of the tool.

* * * * *